(12) United States Patent
Ding et al.

(10) Patent No.: US 11,062,796 B2
(45) Date of Patent: Jul. 13, 2021

(54) MULTIMODE MOBILE ELECTRONIC MEDICAL RECORD SYSTEM AND WORKING METHOD THEREOF

(71) Applicant: Hefei University of Technology, Hefei (CN)

(72) Inventors: Shuai Ding, Hefei (CN); Shanlin Yang, Hefei (CN); Wenjuan Fan, Hefei (CN); Feng Niu, Hefei (CN); Zeyuan Wang, Hefei (CN); Ling Li, Hefei (CN); Zijie Yue, Hefei (CN)

(73) Assignee: Hefei University of Technology, Hefei (CN)

( * ) Notice: Subject to any disclaimer, the term of this patent is extended or adjusted under 35 U.S.C. 154(b) by 0 days.

(21) Appl. No.: 15/803,166

(22) Filed: Nov. 3, 2017

(65) Prior Publication Data
US 2018/0137246 A1    May 17, 2018

(30) Foreign Application Priority Data
Nov. 15, 2016    (CN) .......................... 201611004893.2

(51) Int. Cl.
*G16H 10/60* (2018.01)
*H04L 29/08* (2006.01)
(Continued)

(52) U.S. Cl.
CPC ............. *G16H 10/60* (2018.01); *H04L 63/08* (2013.01); *H04L 67/04* (2013.01); *H04L 67/06* (2013.01);
(Continued)

(58) Field of Classification Search
CPC .. G06Q 50/22–24; G06Q 10/10; G06Q 50/24; G16H 10/60; H04L 63/0853; G06F 19/321; G06F 8/24
See application file for complete search history.

(56) References Cited

U.S. PATENT DOCUMENTS 8,588,765 B1 * 11/2013 Harrison ................ G16H 10/60
455/424
2005/0132269 A1 * 6/2005 Chakraborty ........... G06F 16/58
715/239
(Continued)

FOREIGN PATENT DOCUMENTS

| CN | 102231172 A | 11/2011 |
|---|---|---|
| CN | 105678671 A | 6/2016 |
| CN | 205608810 U | 9/2016 |

*Primary Examiner* — Robert W Morgan
*Assistant Examiner* — Edward B Winston, III

(57) ABSTRACT

The present invention discloses a multimode mobile electronic medical record system and a working method thereof. The multimode mobile electronic medical record system comprises a plurality of mobile terminals, service server, push server, authentication server and cloud server. The mobile terminal comprises a medical record information collection module, a medical record generation module, a medical record synchronization module, a medical record parsing module and a medical record showing module. The service server comprises a medical record storage module and a medical record exchange module. The push server comprises a medical record push module. The authentication server comprises a medical record safety control module. The multimode mobile electronic medical record system can meet collection, integration and transfer of multimode electronic medical record information in a mobile medical environment, and can efficiently improve efficiency and convenience of mobile medical services.

1 Claim, 3 Drawing Sheets

(51) Int. Cl.
*H04L 29/06* (2006.01)
*H04W 12/06* (2021.01)

(52) U.S. Cl.
CPC ...... *H04L 67/1095* (2013.01); *H04L 67/1097* (2013.01); *H04L 67/26* (2013.01); *H04W 12/06* (2013.01); *H04L 67/42* (2013.01)

(56) References Cited

U.S. PATENT DOCUMENTS

| | | | | |
|---|---|---|---|---|
| 2009/0094014 | A1* | 4/2009 | Crisman | G06F 8/24 |
| | | | | 703/16 |
| 2010/0228559 | A1* | 9/2010 | Boone | G16H 15/00 |
| | | | | 705/1.1 |
| 2013/0191161 | A1* | 7/2013 | Churchwell | G16H 10/60 |
| | | | | 705/3 |
| 2014/0100885 | A1* | 4/2014 | Stern | G16H 50/30 |
| | | | | 705/3 |
| 2017/0311159 | A1* | 10/2017 | Tulliano | H04M 1/72415 |

* cited by examiner

MULTIMODE MOBILE ELECTRONIC MEDICAL RECORD SYSTEM AND WORKING METHOD THEREOF

TECHNICAL FIELD

The present invention relates to the field of mobile medical technology, and particularly to a multimode mobile electronic medical record system and a working method thereof.

BACKGROUND

With the rapid development of mobile internet and smart handheld terminals, mobile medical care has become one of the currently hottest focuses. The mobile medical care provides medical services and information through portable mobile devices and wireless communication technology. An electronic medical record (EMR), which is an important part of the mobile medical care, is an important carrier for recording patient's personal history information and an important reference point for doctors to diagnose. However, the electronic medical record used in the current mobile medical care still has the following problems to be solved:

1, the structured organization of a multimode mobile electronic medical record. The collection of mobile electronic medical record information is finished by mobile terminals while the mobile electronic medical record usually comprises multi-source and heterogeneous information such as texts, voice, images, videos and the like and how to organize these semi-structured and unstructured information reasonably and efficiently in a structured manner in the mobile terminals will have great effect on efficiencies in the storage and network transmission of the mobile electronic medical record.

2, the storage of the mobile electronic medical record. The mobile electronic medical record, which is an internet service essentially, is different from electronic medical record services in an ordinary LAN environment. A reasonable storage strategy is one of important factors to ensure the service stability of an electronic medical record system in a large-capacity and high-concurrent network environment since image information such as large-size images and videos is present in the mobile electronic medical record.

3, the synchronization and push of the mobile electronic medical record. At present, in the field of mobile medical field in China, some mobile medical products have already been able to provide mobile electronic medical record services. However, these mobile electronic medical record services are currently only at the level of the visualized presentation of electronic medical record mobile terminals and have not yet taken into account the unique advantages of the mobile terminals: synchronization and push, that is, real-time synchronization of electronic medical records between mobile terminals and server terminals and the instant push of medical records between doctors and patients.

4, The standardized conversion of the mobile electronic medical record. Mobile electronic medical record information is derived from mobile terminals such that image information such as pictures and videos collected by different mobile terminals may have different coding standards, which will result in that mobile electronic medical records generated in the current platform cannot be exchanged with the mobile electronic medical records in other electronic medical record systems, thereby reducing the universality in the use of the current medical record system.

SUMMARY

In order to overcome the defects in the prior art, the present invention provides a multimode mobile electronic medical record system capable of realizing collection, integration and transfer of multimode electronic medical record information in a mobile medical environment, thereby efficiently improving efficiency and convenience of mobile medical services, and working method thereof.

In accordance with the present invention, the following technical solution is adopted to solve the technical problems above.

The multimode mobile electronic medical record system according to the present invention comprises mobile terminals, service server, push server, authentication server and cloud server.

The mobile terminal comprises a medical record information collection module, a medical record generation module, a medical record synchronization module, a medical record parsing module and a medical record showing module.

The service server comprises a medical record storage module and a medical record exchange module.

The push server comprises a medical record push module.

The authentication server comprises a medical record safety control module.

The medical record information collection module acquires medical record information according to a standardized electronic medical record template and provides it to the medical record generation module, wherein the medical record information comprises text-based basic information of a patient, patient's complaints, medical history information, diagnosis information, text-based or voice-based information of doctor's advices and picture-based or video-based information of medical image.

The medical record generation module builds standardized description for the medical record information, and thereby obtain an electronic medical record comprising a medical record description file and a medical record resource file.

The medical record synchronization module compresses the electronic medical record and synchronizes it to the service server; at the same time, the medical record synchronization module sends a medical record synchronization request initiated by the mobile terminal to the authentication server for verifying identity and authority, after the verification is passed, the medical record safety control module forwards the medical record synchronization request to the service server for synchronizing the electronic medical record from the service server to the mobile terminal.

The medical record storage module of the service server receives the compressed electronic medical record for local storage and uploads the medical record resource file to the cloud server for storage and access.

The medical record parsing module of the mobile terminal parses the electronic medical record sent by the medical record synchronization module, obtains the medical record information and displays it through the medical record showing module.

The mobile terminal selects a desired electronic medical record from the medical record showing module and sends a medical record push request to the service server.

The service server converts the received medical record push request into a push record and sends it to the push server.

The medical record push module sequentially generates a medical record push queue according to the received push record and sends push information to other mobile terminal.

The other mobile terminal obtains a corresponding electronic medical record from the medical record storage module according to the push information, thereby completing the push of the electronic medical record; and The medical record exchange module performs encoding format conversion on the electronic medical record to obtain a medical record with a common format for exchanging the medical record with an external medical record system.

The multimode mobile electronic medical record system according to the present invention is characterized in that the medical record storage module comprises a receiving unit, a decompressing unit, an uploading unit, an updating unit and a storage unit.

The receiving unit receives the electronic medical record and decompress it by the decompressing unit to obtain an electronic medical record.

The uploading unit uploads a medical record resource file in the electronic medical record to the cloud server and records the absolute path of the medical record resource file stored in the cloud server.

The updating unit adds a urls tag below the tag corresponding to the medical record description file according to the type of the medical record resource file for storing the absolute path.

The storage unit distributes a corresponding storage space for the current medical record, and stores the medical record description file with the urls tag and the medical record resource file.

A working method of the multimode mobile electronic medical record system according to the present invention is applied to a system consisting of mobile terminals, service server, push server, authentication server and cloud server, and is carried out according to the following steps:

step 1: acquiring medical record information by the mobile terminal comprising text-based basic information of a patient, patient's complaints, medical history information, diagnosis information, text-based or voice-based information of doctor's advices and picture-based or video-based information of medical image;

step 2: describing the medical record information by the mobile terminal based on XML to obtain an XML-based electronic medical record comprising a medical record description file and a medical record resource file;

step 3: compressing the electronic medical record and synchronizing the electronic medical record by the mobile terminal to the service server;

step 4: receiving the compressed electronic medical record by the service server for local storage and uploads the medical record resource file to the cloud server for storage and access;

step 4.1: receiving the electronic medical record and decompressing the electronic medical record by the service server to obtain an electronic medical record;

step 4.2: uploading the medical record resource file in the electronic medical record to the cloud server and recording the absolute path of the medical record resource file stored in the cloud server;

step 4.3: adding a urls tag to the medical record description file for storing the absolute path;

step 4.4: distributing a corresponding storage space for the current medical record, and storing the medical record description file with the urls tag and the medical record resource file;

step 5: sending the acquired medical record synchronization request to the authentication server by the mobile terminal for verifying identity and authority;

step 6: forwarding the medical record synchronization request passed by the verification from the authentication server to the service server;

step 7: acquiring the corresponding electronic medical record by the service server in terms of the medical record synchronization request and synchronizing the corresponding electronic medical record to the mobile terminal;

step 8: performing XML-based reverse format parser on the electronic medical record synchronously downloaded from the service server by the mobile terminal to obtain the medical record description file with the urls tag;

step 9: acquiring the absolute path of the medical record resource file according to the urls tag by the mobile terminal and downloading asynchronously the corresponding medical record resource file from the cloud server according to the absolute path, thereby displaying the medical record information;

step 10: selecting the desired electronic medical record and sending a medical record push request from the mobile terminal to the service server;

step 11: converting the received medical record push request by the service server into a push record and sends the push record to the push server;

step 12: sequentially generating a medical record push queue by the push server according to the push record and sending push information to a target mobile terminal based on a Message Queuing Telemetry Transport (MQTT) information transport protocol;

step 13: acquiring a corresponding electronic medical record from the service server by the target mobile terminal according to the push information, thereby completing the push of the electronic medical record; and step 14: further performing an encoding format conversion on the medical record description file by the service server based on an Health Level Seven-Clinical Document Architecture (HL7CDA) protocol and on the medical record resource file in the electronic medical record based on a Digital Imaging and Communications in Medicine (DICM) protocol, thereby obtaining the medical record with a common format for exchanging the medical record with an external medical record system.

Compared with the prior art, the invention has the beneficial effects as follows:

1, in the multimode mobile electronic medical record system and the working method thereof according to the present invention, firstly, information on the mobile electronic medical record is collected and described by standard by the medical record information collection module and the medical record generation module to generate a standardized file; secondly, the synchronous uploading and downloading of the mobile electronic medical record is achieved by the medical record synchronization module; the efficiency of the access to the mobile electronic medical record is enhanced by using a distributed cloud storage strategy in the medical record storage module; in a medical record push module, the push service of the mobile electronic medical record between the terminals is completed through the push server; in the medical record exchange module, the format of the mobile electronic medical record is converted according to the common encoding protocol within the medical field; in the medical record safety control module, the safety of the access to the mobile electronic medical record is ensured by verifying identity and access permissions. Through the above-mentioned main functional modules, the collection, integration and transfer of multimode electronic medical record information in a mobile medical environment are completed, thereby efficiently improving efficiency and convenience of mobile medical services.

2, in the multimode mobile electronic medical record system and the working method thereof according to the present invention, the medical record information collection module collects the medical record information through the mobile terminal, while the medical record information presents multimodal and heterogeneous characteristics. Therefore, in order to solve the problem, an XML-based medical record file structure is defined in the medical record generation module of the system and the medical record information is described by standard by the file structure, thereby obtaining a medical record description file and a medical record resource file. Finally, it completes the structural description of an unstructured mobile electronic medical record.

3, in the multimode mobile electronic medical record system and the working method thereof according to the present invention, in order to solve the problem of the synchronization of the mobile electronic medical record, the electronic medical record is compressed and then synchronized to the service server in the medical record synchronization module. At the same time, the medical record synchronization module sends a medical record synchronization request initiated by the mobile terminal to the service server, thereby synchronizing the electronic medical record from the service server to the mobile terminal.

4, in the multimode mobile electronic medical record system and the working method thereof according to the present invention, in order to improve the access efficiency of the mobile electronic medical record, the distributed storage strategy is adopted in the medical record storage module of the system to upload the resource file with larger size in the medical record to the cloud server with the higher bandwidth, so that the access efficiency of the medical record information can be effectively improved while the pressure on the local server is relieved and the user experience is also enhanced.

5, in the multimode mobile electronic medical record system and the working method thereof according to the present invention, in order to solve the instant push of the mobile electronic medical record, the push server is built the in the medical record push module of the system and the push server sequentially generates a medical record push queue according to the push record and sends the push information to the target mobile terminal based on the MQTT information transport protocol, thereby achieving the push of the mobile electronic medical record between the terminals.

6, in the multimode mobile electronic medical record system and the working method thereof according to the present invention, in order to solve the problem of exchanging the mobile electronic medical record with an external electronic medical record system, the service server performs encoding format conversion on the medical record description file based on the HL7CDA protocol and on the medical record resource file in the electronic medical record based on the DICM protocol, thereby obtaining the medical record with a common format for exchanging the medical record with an external medical record system.

DETAILED DESCRIPTION

Figure 1:
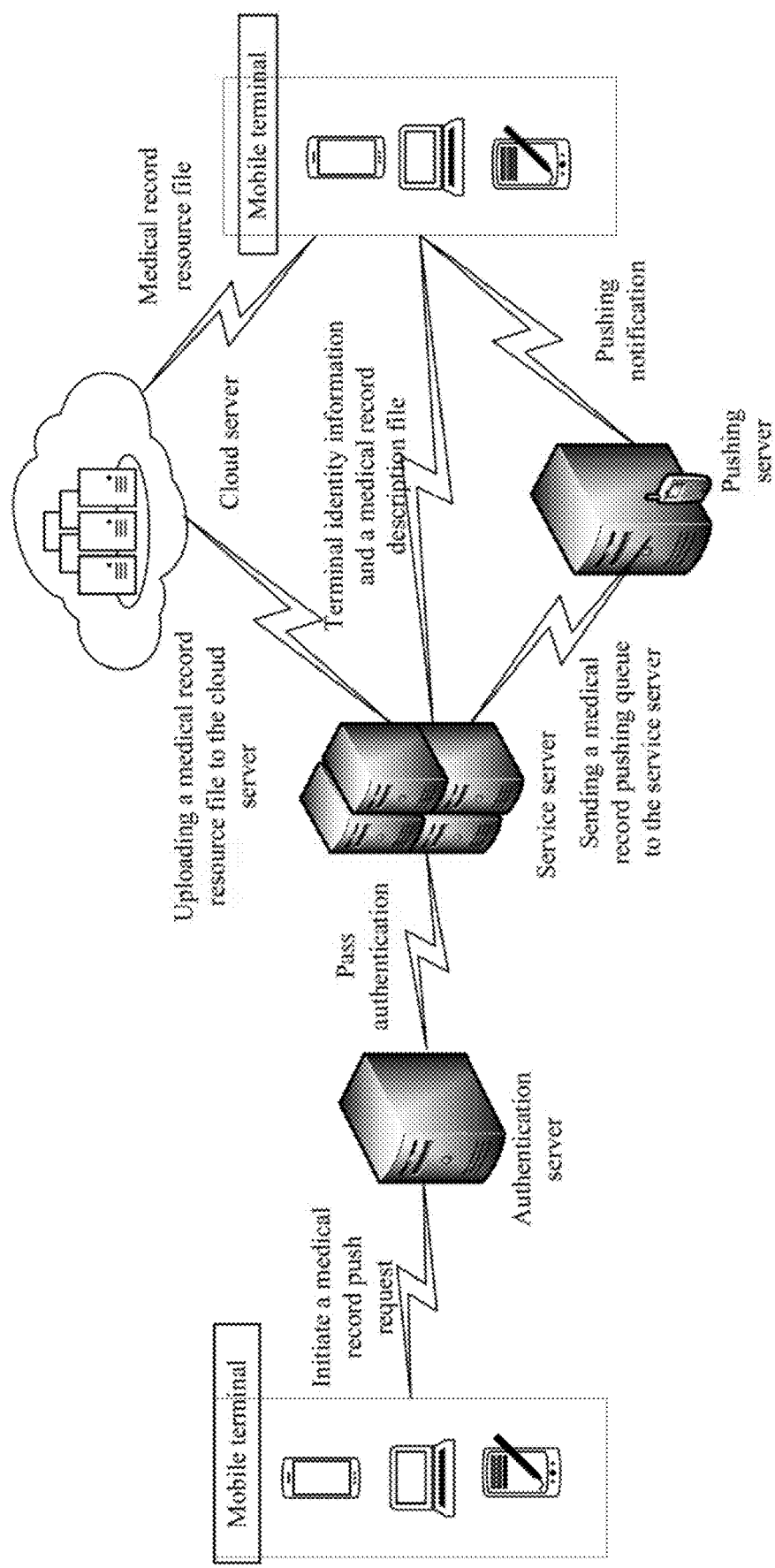
FIG. 1 is a basic flow chart in accordance with the present invention.

In the present embodiment, a multimode mobile electronic medical record system is provided with a system architecture comprising: mobile terminals, service server, push server, authentication server and cloud server as shown in FIG. 1.

Figure 2:
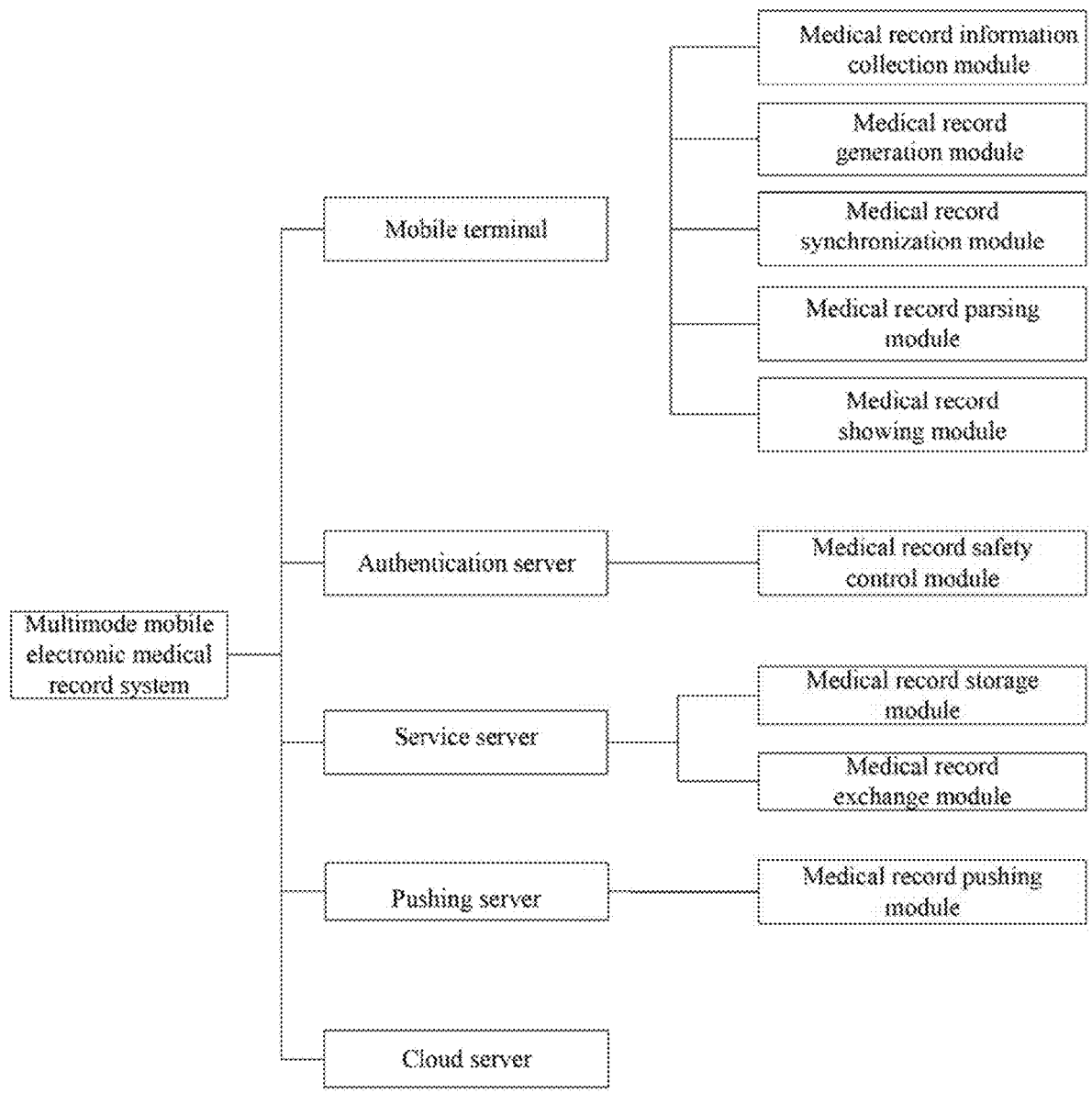
FIG. 2 is a schematic diagram illustrating the structure of the system in accordance with the present invention.

The mobile terminal refers to terminal applications installed on a smart phone, a tablet computer and a dedicated handheld device. It is mainly configured to collect and describe the multimode electronic medical record information by standard and then synchronize the described medical record information to the service server. The mobile terminal synchronizes the medical record information on the service server to the local and performs reverse analysis and visualized showing on the medical record. As shown in FIG. 2, the mobile terminal includes a medical record information collection module, a medical record generation module, a medical record synchronization module, a medical record parsing module, a medical record showing module.

The service server is configured to complete the logical processing of the electronic medical record in the background. It is mainly configured to perform distributed storage on the electronic medical record synchronized to the mobile terminal by the mobile terminal and convert the electronic medical record according to a standard format, thereby obtaining a general electronic medical record for exchanging with the other medical record systems. As shown in FIG. 2, the service server includes a medical record storage module and a medical record exchange module.

The push server is configured to achieve the push of the mobile electronic medical record between the mobile terminals, mainly generate a corresponding medical record push queue in response to a medical record push request initiated by the mobile terminal, and finally complete the push service by the push server. The push server includes a medical record push module.

The authentication server is configured to complete the safety access control over the mobile electronic medical record, mainly to authenticate the identity and authority of the mobile terminal, thereby protecting the privacy information in the medical record. The authentication server includes a medical record safety control module.

The medical record information collection module acquires medical record information according to a standardized electronic medical record template and provides it to the medical record generation module, wherein the medical record information comprises text-based basic information of a patient, patient's complaints, medical history information, diagnosis information, text-based or voice-based information of doctor's advices and picture-based or video-based information of medical image, wherein the sources of the medical record information comprise:

(1) the patient, doctor's information and basic information of a user using the current electronic medical record system, which are imported automatically into the medical record;

(2) patient's complaints, medical history information and basic information filled by the user when making an appointment with the doctor, which are imported automatically into the medical record;

(3) information of diagnosis and medical orders, which are filled and recorded by the doctor in the mobile terminal in his/her own, and (4) a check report and medical images, which are generated by mobile medical examination equipment and imported automatically into the medical record.

Figure 3:
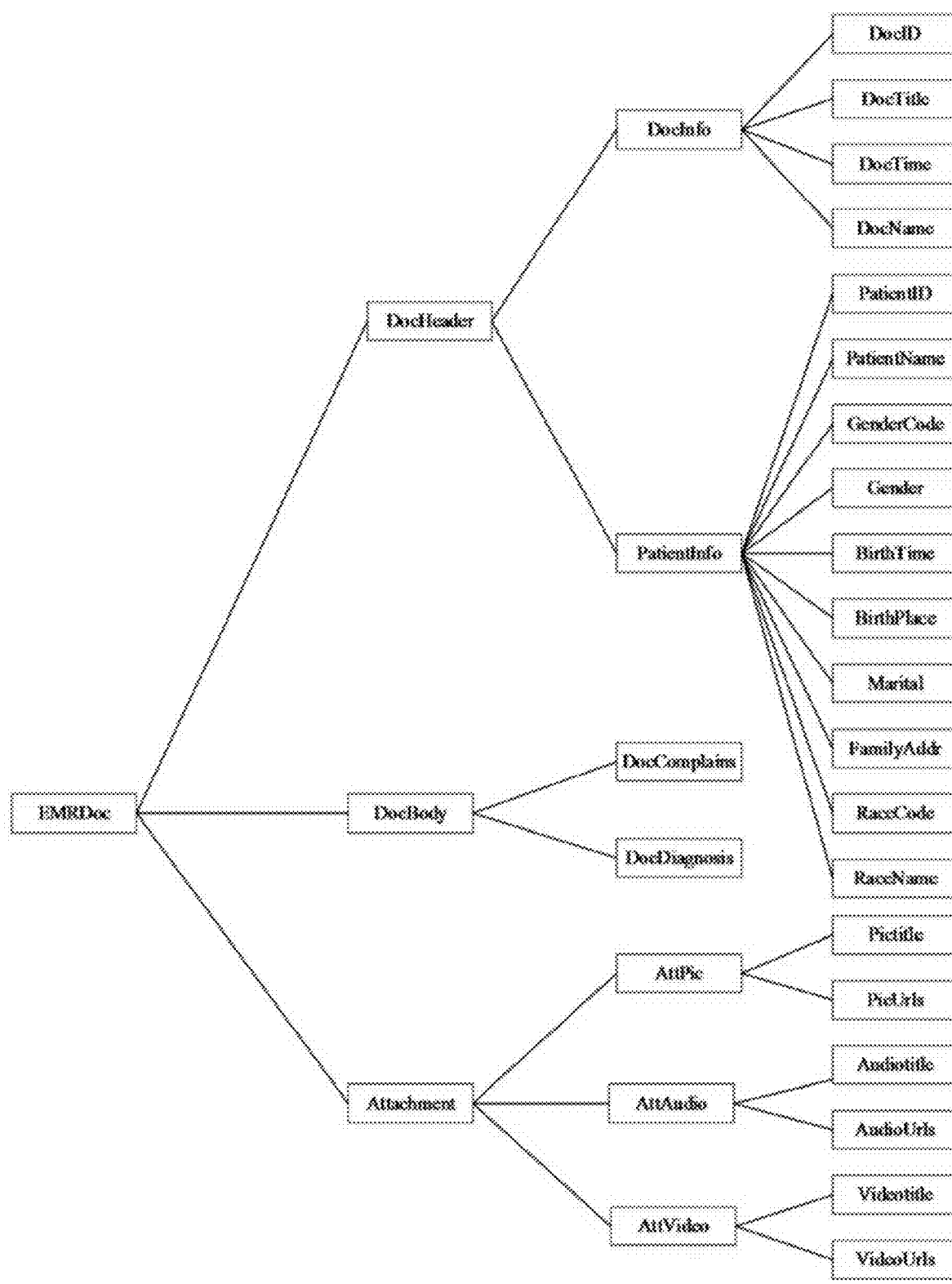
FIG. 3 is a schematic diagram illustrating the structure of the electronic medical record template in accordance with the present invention.

As shown in FIG. 3, the structure of an XML-based medical record file consists mainly of DocHeader, DocBody and Attachment. DocBeader is mainly configured to describe the patient' and the doctor's information and consists of DocInfo and PatientInfo; DocBody is mainly configured to describe patient's complaints and diagnosis information by the doctor and consists of DocComplains and DocDiagnosis; and Attachment is mainly configured to store the path of the medical record resource file and consists of AttPic, AttAudio and AttVideo.

The medical record generation module is configured to adopt the XML-based medical record file structure to describe the medical record information by standard, thereby obtaining an electronic medical record comprising a medical record description file and a medical record resource file.

In consideration of larger number of files and larger sizes of the files during the synchronization of the medical records to the service server, in order to prevent the medical record file from being lost, the electronic medical record is synchronized to the service server after being compressed in the medical record synchronization module; At the same time, the medical record synchronization module sends a medical record synchronization request initiated by the mobile terminal to the authentication server for verifying identity and authority, after the verification is passed, the medical record safety control module forwards the medical record synchronization request to the service server for synchronizing the electronic medical record from the service server to the mobile terminal; the medical record synchronization module comprises synchronized uploading and downloading of the medical record which comprise the following steps:

(1) performing bidirectional mapping on an ID index table of the medical record at the mobile terminal and service server;

(2) automatically generating a task queue for synchronizing the medical record according to the mapping results; and (3) completing the synchronization of the medical record according to the task queue.

The authentication server is configured to check the validation of the mobile terminal's identity and access authority, thereby realizing the safety control over the access to the mobile electronic medical record system. The stored information comprises information on the mobile terminal's identity and the access control strategy, wherein the information on the mobile terminal's identity consists of a user name, a keyword and Token with time-validity and the access control strategy consists of RBAC access control strategy designed by experts and a personalized strategy made by patients and doctors. The medical record safety control module performs following steps:

(1) sending a medical record synchronization request by the mobile terminal;

(2) intercepting the medical record request and analyzing the request by the authentication server; and (3) verifying the validation of the mobile terminal's identity and access authority and forwarding the request to the service server for processing after the verification is passed.

In consideration that the access to the medical record in the high-capacity and high concurrent network request environment will make the service server bear higher pressure so that the service server cannot be guaranteed to provide efficient and stable service, the medical record storage module of the service server receives the compressed electronic medical record for local storage and uploads the medical record resource file with larger size to the cloud server for storage and access. In this way, the access efficiency of the terminal is improved using the high bandwidth of the cloud server and the pressure on the service server is reduced.

The medical record parsing module of the mobile terminal performs inverse XML format parser on the electronic medical record sent by the medical record synchronization module, obtains the medical record information and displays it through the medical record showing module.

The mobile terminal selects a desired electronic medical record from the medical record showing module and sends a medical record push request to the service server; and the service server converts the received medical record push request into a push record and sends it to the push server.

The medical record push module sequentially generates a medical record push queue according to the received push record and sends push information to other mobile terminal; in the medical record push module, the MQTT protocol is selected to achieve the push of the medical record information from the aspects of the difficulty in achievement and the network loss, that is, the MQTT protocol is adopted to perform the push of message data; the mobile terminal and push server maintain a long-lived connection through the MQTT protocol so as to ensure the mobile terminal to receive the medical record information pushed by the push server in real time.

The other mobile terminal obtains a corresponding electronic medical record from the medical record storage module according to the push information, thereby completing the push of the electronic medical record.

In order to realize the exchange of heterogeneous electronic medical records between different electronic medical record systems, the medical record exchange module performs encoding format conversion on the stored electronic medical record, that is, performs encoding format conversion on the medical record description file based on the HL7CDA protocol and on the medical record resource file in the electronic medical record based on the DICM protocol and finally obtains the medical record with a common format for exchanging the medical record with an external medical record system.

In the present embodiment, the medical record storage module comprises a receiving unit, a decompressing unit, an uploading unit, an updating unit and a storage unit.

The receiving unit receives the electronic medical record and decompress it by the decompressing unit to obtain an electronic medical record comprising a medical record description file and a medical record resource file.

The uploading unit uploads the medical record resource file in the electronic medical record to the cloud server and records the absolute path of the medical record resource file stored in the cloud server.

the updating unit adds a urls tag below different nodes (AttPic, AttAudio and AttVideo) in the XML-based medical record description file according to the type of the medical record resource file for storing the absolute path of the medical record; and The storage unit distributes a corresponding storage space for the current medical record, and stores the medical record description file with the urls tag and the medical record resource file.

In the present embodiment, a working method of the multimode mobile electronic medical record system is applied to a system consisting of mobile terminals, service server, push server, authentication server and cloud server. Information on a mobile electronic medical record is collected and described by standard, compressed through the mobile terminal and synchronized to the service server through the network, the service server receives the electronic medical record information, decompresses, performs the distributed storage, and updates a medical record description file; the mobile terminal initiates a medical record push request, the service server receives the push request, generates a medical record push queue and transports it to the push server; the push server completes the push task of the medical record information to the mobile terminal; the mobile terminal sends a synchronization request to the service server, synchronizes the medical record to the local, performs reverse XML format parser and completes the visualized showing of the medical record. Throughout the process, the authentication server checks the validation of the mobile terminal's identity and access authority in real time. At the same time, for the electronic medical record stored in the service server, a medical record with a common format is generated through encoding format conversion for exchanging with other medical records. The flow of the entire method is carried out as follows:

step 1: acquiring medical record information by the mobile terminal comprising text-based basic information of a patient, patient's complaints, medical history information, diagnosis information, text-based or voice-based information of doctor's advices and picture-based or video-based information of medical image;

step 2: describing the medical record information by the mobile terminal based on XML to obtain an XML-based electronic medical record comprising a medical record description file and a medical record resource file;

step 3: compressing the electronic medical record and synchronizing the electronic medical record by the mobile terminal to the service server;

step 4: receiving the compressed electronic medical record by the service server for local storage and uploads the medical record resource file to the cloud server for storage and access;

step 4.1: receiving the electronic medical record and decompressing the electronic medical record by the service server to obtain an electronic medical record;

step 4.2: uploading the medical record resource file in the electronic medical record to the cloud server and recording the absolute path of the medical record resource file stored in the cloud server;

step 4.3: adding a urls tag to the medical record description file for storing the absolute path;

step 4.4: distributing a corresponding storage space for the current medical record, and storing the medical record description file with the urls tag and the medical record resource file;

step 5: sending the acquired medical record synchronization request to the authentication server by the mobile terminal for verifying identity and authority;

step 6: forwarding the medical record synchronization request passed by the verification from the authentication server to the service server;

step 7: acquiring the corresponding electronic medical record by the service server in terms of the medical record synchronization request and synchronizing the corresponding electronic medical record to the mobile terminal;

step 8: performing XML-based reverse format parser on the electronic medical record synchronously downloaded from the service server by the mobile terminal to obtain the medical record description file with the urls tag;

step 9: acquiring the absolute path of the medical record resource file according to the urls tag by the mobile terminal and downloading asynchronously the corresponding medical record resource file from the cloud server according to the absolute path, thereby displaying the medical record information;

step 10: selecting the desired electronic medical record and sending a medical record push request from the mobile terminal to the service server;

step 11: converting the received medical record push request by the service server into a push record and sends the push record to the push server;

step 12: sequentially generating a medical record push queue by the push server according to the push record and sending push information to a target mobile terminal based on a Message Queuing Telemetry Transport (MQTT) information transport protocol;

step 13: acquiring a corresponding electronic medical record from the service server by the target mobile terminal according to the push information, thereby completing the push of the electronic medical record; and step 14: further performing an encoding format conversion on the medical record description file by the service server based on the HL7CDA protocol and on the medical record resource file in the electronic medical record based on the DICM protocol, thereby obtaining the medical record with a common format for exchanging the medical record with an external medical record system.

What is claimed is:

1. A working method of a multimode mobile electronic medical record system comprising a plurality of mobile terminals, a service server, a push server, an authentication server and a cloud server, the working method comprising:
 step 1: acquiring medical record information by the mobile terminal comprising text-based basic information of a patient, patient's complaints, medical history information, diagnosis information, text-based or voice-based information of doctor's advices and picture-based or video-based information of medical image, comprising importing the basic information and the medical history information from an existing electronic medical record, acquiring the doctor's advice and diagnosis information entered into the mobile terminal by doctors, and automatically importing check reports and medical images from mobile medical examination equipment;
 step 2: describing the medical record information by the mobile terminal based on XML to obtain an XML-based electronic medical record comprising a medical record description file and a medical record resource file;
 step 3: performing bidirectional mapping on an ID index table of the medical record at the mobile terminal and the service server; automatically generating a task queue for synchronizing the medical record according to the mapping; and compressing the electronic medical record and synchronizing the electronic medical record by the mobile terminal to the service server according to the task queue;

step 4: receiving the compressed electronic medical record by the service server for local storage and uploading the medical record resource file to the cloud server for storage and access;

step 4.1: receiving the electronic medical record and decompressing the electronic medical record by the service server to obtain an electronic medical record;

step 4.2: uploading the medical record resource file in the electronic medical record to the cloud server and recording an absolute path of the medical record resource file stored in the cloud server;

step 4.3: adding a urls tag to the medical record description file for storing the absolute path;

step 4.4: distributing a corresponding storage space for the current medical record, and storing the medical record description file with the urls tag and the medical record resource file;

step 5: sending the acquired medical record synchronization request to the authentication server by the mobile terminal for verifying identity and authority;

step 6: forwarding the medical record synchronization request passed by the verification from the authentication server to the service server;

step 7: acquiring the corresponding electronic medical record by the service server in terms of the medical record synchronization request and synchronizing the corresponding electronic medical record to the mobile terminal;

step 8: performing XML-based reverse format parser on the electronic medical record synchronously downloaded from the service server by the mobile terminal to obtain the medical record description file with the urls tag;

step 9: acquiring the absolute path of the medical record resource file according to the urls tag by the mobile terminal and downloading asynchronously the corresponding medical record resource file from the cloud server according to the absolute path, thereby displaying the medical record information;

step 10: selecting the desired electronic medical record and sending a medical record push request from the mobile terminal to the service server;

step 11: converting the received medical record push request by the service server into a push record and sends the push record to the push server;

step 12: sequentially generating a medical record push queue by the push server according to the push record and sending push information to a target mobile terminal based on a Message Queuing Telemetry Transport (MQTT) information transport protocol;

step 13: acquiring a corresponding electronic medical record from the service server by the target mobile terminal according to the push information, thereby completing the push of the electronic medical record; and step 14: further performing an encoding format conversion on the medical record description file by the service server based on an Health Level Seven-Clinical Document Architecture (HL7CDA) protocol and on the medical record resource file in the electronic medical record based on a Digital Imaging and Communications in Medicine (DICM) protocol, thereby obtaining the medical record with a common format for exchanging the medical record with an external medical record system.

* * * * *